United States Patent [19]

Takago et al.

[11] Patent Number: 4,891,434

[45] Date of Patent: Jan. 2, 1990

[54] NOVEL ORGANOSILICON COMPOUND

[75] Inventors: Toshio Takago; Masatoshi Arai; Koji Futatsumori, all of Gunma, Japan

[73] Assignee: Shin-Etsu Chemical Co., Ltd., Tokyo, Japan

[21] Appl. No.: 120,249

[22] Filed: Nov. 10, 1987

Related U.S. Application Data

[63] Continuation of Ser. No. 829,290, Feb. 13, 1986, abandoned.

[30] Foreign Application Priority Data

Feb. 15, 1985 [JP] Japan ................................. 60-27979

[51] Int. Cl.$^4$ ........................................... C07D 303/02
[52] U.S. Cl. .................................................... 549/215
[58] Field of Search ........................................ 549/215

[56] References Cited

U.S. PATENT DOCUMENTS

| | | | |
|---|---|---|---|
| 3,455,877 | 7/1969 | Plueddemann | 549/215 |
| 3,485,780 | 12/1969 | Sterman et al. | 549/215 |
| 3,887,487 | 6/1975 | Camp et al. | 549/215 |
| 3,971,747 | 7/1976 | Bank et al. | 549/215 |
| 3,998,991 | 12/1976 | Kaas | 549/215 |

FOREIGN PATENT DOCUMENTS 3023622  1/1981  Fed. Rep. of Germany.

OTHER PUBLICATIONS

E. P. Plueddemann et al., Jour. Am. Chem. Soc., vol. 81, (1959), pp. 2632–2635.

Primary Examiner—Catherine L. Mills
Attorney, Agent, or Firm—Jules E. Goldberg

[57] ABSTRACT

The invention discloses a novel class of organosilane compounds containing 1 to 3 alkenyloxy groups directly bonded to the silicon atom and a 3,4-epoxycyclohexyl-substituted alkyl group bonded to the silicon atom. The compound is prepared by the reaction of 1-vinyl-3,4-epoxycyclohexane and a hydrogen alkenyloxy silane and useful as a coupling agent or an adhesion-improving agent.

3 Claims, 2 Drawing Sheets

NOVEL ORGANOSILICON COMPOUND

This is a continuation of application Ser. No. 829,290, filed Feb. 13, 1986.

BACKGROUND OF THE INVENTION

The present invention relates to a novel organsilicon compound never described in any of previous literatures or published documents or, in particular, to a class of novel organosilane compounds with an epoxy group bonded to the silicon atom in the form of a 3,4-epoxycyclohexyl group and at least one alkenyloxy group directly bonded to the silicon atom in a molecule. These compounds are useful as a coupling agent or an adhesion-improving agent owing to the high reactivity thereof.

SUMMARY OF THE INVENTION

The novel organosilicon compound or organosilane compound of the invention is a compound represented by the general formula

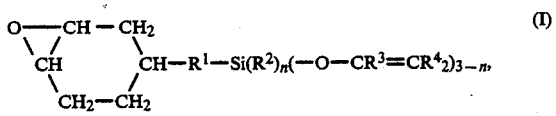

in which $R^1$ is a divalent hydrocarbon group having 2 to 5 carbon atoms, $R^2$, $R^3$ and $R^4$ are each a hydrogen atom or a monovalent hydrocarbon group having 1 to 8 carbon atoms and the subscript n is 0, 1 or 2.

DETAILED DESCRIPTION OF THE PREFERRED EMBODIMENTS

Figure 1:
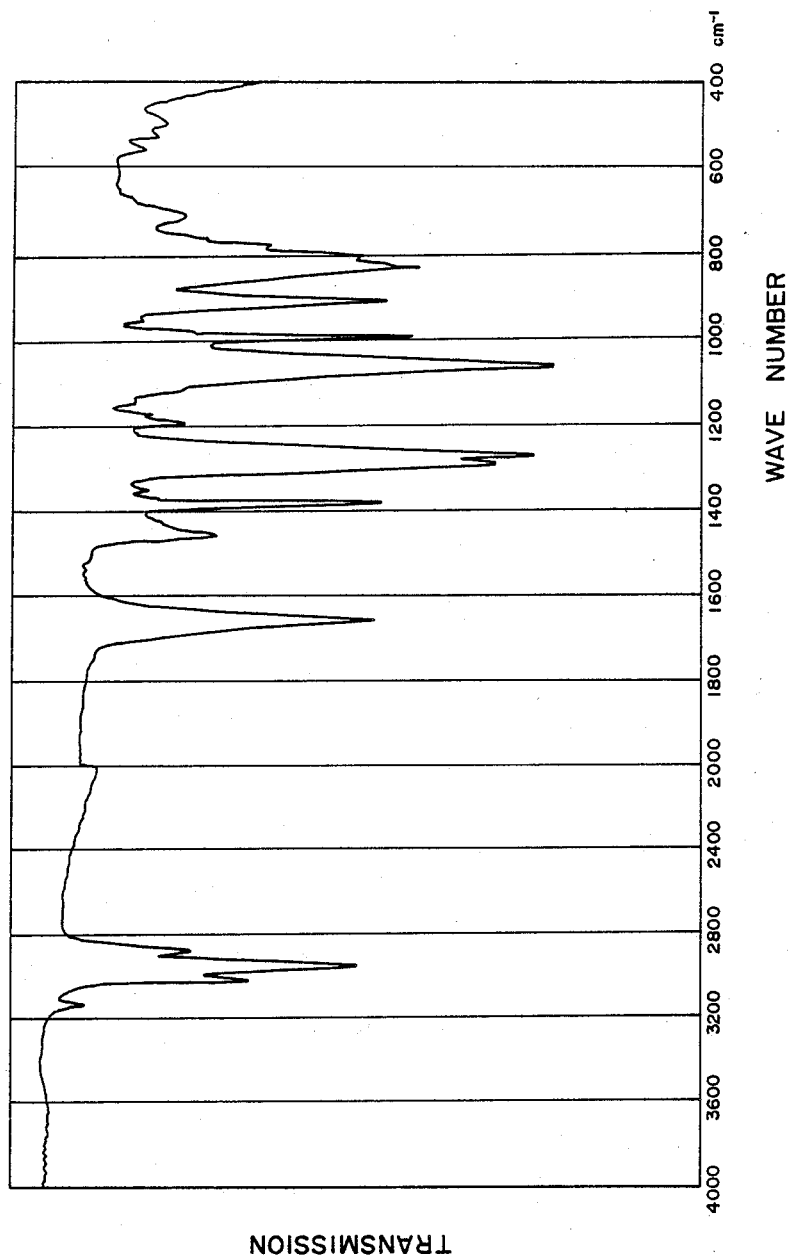
FIGS. 1 and 2 each show an infrared absorption spectrum of the compound prepared in Examples 1 and 2, respectively.

The organosilicon or organosilane compound of the present invention is represented by the above given general formula (I), in which each of the symbols $R^1$, $R^2$, $R^3$, $R^4$ and n has the meaning as defined above. The divalent hydrocarbon group having 2 to 5 carbon atoms denoted by the symbol $R^1$ is exemplified by those expressed by the following structural formulas: —CH$_2$CH$_2$—; —CH(CH$_3$)—; —CH—CH(CH$_3$)—; —CH$_2$CH$_2$CH$_2$— and —CH$_2$CH$_2$CH$_2$CH$_2$CH$_2$—. $R^2$ denotes a hydrogen atom or a substituted or unsubstituted monovalent hydrocarbon group having 1 to 8 carbon atoms. When the compound has two groups of $R^2$ in a molecule, they can be either of the same kind or of different kinds from each other. The hydrocarbon group denoted by $R^2$ is selected from the class consisting of alkyl groups, e.g. methyl, ethyl, propyl and butyl groups, alkenyl groups, e.g. vinyl and allyl groups, aryl groups, e.g. phenyl and tolyl groups and aralkyl groups, e.g. benzyl group as well as those substituted groups obtained by substituting halogen atoms, cyano groups and the like for a parrt or all of the hydrogen atoms in the above named hydrocarbon groups such as chloromethyl, 3,3,3-trifluoropropyl and cyanomethyl groups. Each of the groups denoted by $R^3$ and $R^4$ is a hydrogen atom or a substituted or unsubstituted monovalent hydrocarbon group having 1 to 8 carbon atoms exemplified by those groups given above as the examples of the group denoted by $R^2$. Each of the groups $R^2$, $R^3$ and $R^4$ in a molecule can be selected independently from the others. The subscript n is a number of 0, 1 or 2.

Particular examples of the organsilicon compound in conformity with the above given definition include those expressed by the structural formulas given below, in which the symbol Me denotes a methyl group:

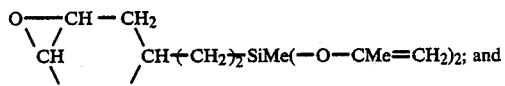

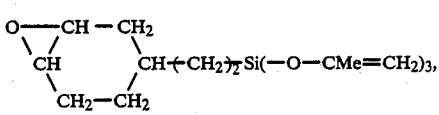

as the typical ones, although the invention is not limited to these particular compounds in any way.

The organosilane compound of the invention can be easily obtained, for example, by the addition reaction between 1-vinyl-3,4-epoxycyclohexane and a hydrogen alkenyloxy silane in the presence of a metal belonging to the VIIIth group of the Periodic Table or a compound thereof as the catalyst. The above-mentioned hydrogen alkenyloxy silane can be prepared by the reaction of a corresponding hydrogen halogenosilane and an α,β-unsaturated aldehyde compound or an α,β-unsaturated ketone compound in the presence of a dehydrohalogenation agent.

The organosilicon compound of the invention is a carbon-functional silane capable of pertaining to a deketonaton type condensation reaction, and the compound exhibits an excellent effect as a coupling agent between an inorganic material and an organic material and also useful in improving the mechanical or electrical properties inherent in epoxy resins, FRPs and the like when it is added thereto. Furthermore, the compound of the invention can be formulated in primer compositions to increase the adhesion-improving effect thereof in combination with a titanium compound such as tetrabutyl titanate and the like or in combination with an isocyanate compound. The compound is also useful for improving the adhesiveness of various curable compositions containing a polyurethane, polysulfide, diorganopolysiloxane, silicone-modified polyoxyalkylene epoxy resin and the like as the principal component on to the material on which the composition has been cured when the inventive compound is added to the composition. Although the curability of curable polyurethane compositions may be sometimes decreased as a whole when the composition is admixed with a conventional dealcoholation-type carbon-functional silane compound such as 2-(3,4-epoxy-cyclohexyl)ethyl trimethoxy silane due to the alcohol liberated during the curing process, the adhesiveness of polyurethane compositions can be advantageously improved without loss of the curability by adding the compound of the invention since the chemical substance liberated during the curing process is a ketone compound in this case.

Examples of the invention are given in the following for the preparation and identification of the inventive compounds.

EXAMPLE 1

Into a reaction vessel were introduced 49.6 g (0.40 mole) of 1-vinyl-3,4-epoxycyclohexane, 60 g of toluene and 0.05 g of an isopropyl alcohol solution of chloroplatinic acid containing 2% by weight of platinum to form a reaction mixture into which 60.2 g (0.38 mole) of methyl diisopropenyloxy silane were added dropwise over a period of 30 minutes while the reaction mixture in the vessel was kept at 60° C. followed by the elevation of the temperature to 80° C. to effect the reaction for 3 hours after the end of the dropwise addition of the silane. By distillation of the reaction mixture after completion of the reaction under reduced pressure, 86.8 g of a liquid fraction boiling at 146° C. under 3 mmHg and having a refractive index of 1.4668 were obtained.

The thus obtained liquid product was subjected to the analysis by the gas chromatographic-mass spectrometric analysis to give a molecular weight of 282 and elementary analysis to give the results shown below and the product could be identified to be an organosilicon compound represented by the formula

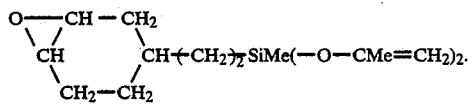

Results of elementary analysis:

|  | C | H | Si |
| --- | --- | --- | --- |
| Calculated as $C_{15}H_{26}O_3Si$, % | 63.83 | 9.22 | 9.93 |
| Found, % | 63.62 | 9.17 | 10.05 |

The above mentioned yield of the product was 81% of the theoretical value. FIG. 1 in the accompanying drawing shows an infrared absorption spectrum of the product.

EXAMPLE 2

The experimental procedure was substantially the same as in Example 1 excepting the use of 65.4 g (0.38 mole) of triisopropenyloxy silane instead of the methyl diisopropenyloxy silane to give 67.7 g of a liquid fraction boiling at 156° C. under 2 mmHg and having a refractive index of 1.4670. This product could be identified to be a compound expressed by the formula

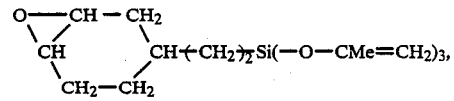

from the gas chromatographic-mass spectrometric analysis to give a molecular weight of 324 and the results of the elementary analysis given below.

Results of elementary analysis:

|  | C | H | Si |
| --- | --- | --- | --- |
| Calculated as $C_{17}H_{28}O_4Si$, % | 62.96 | 8.64 | 8.64 |
| Found, % | 62.85 | 8.60 | 8.71 |

Figure 2:
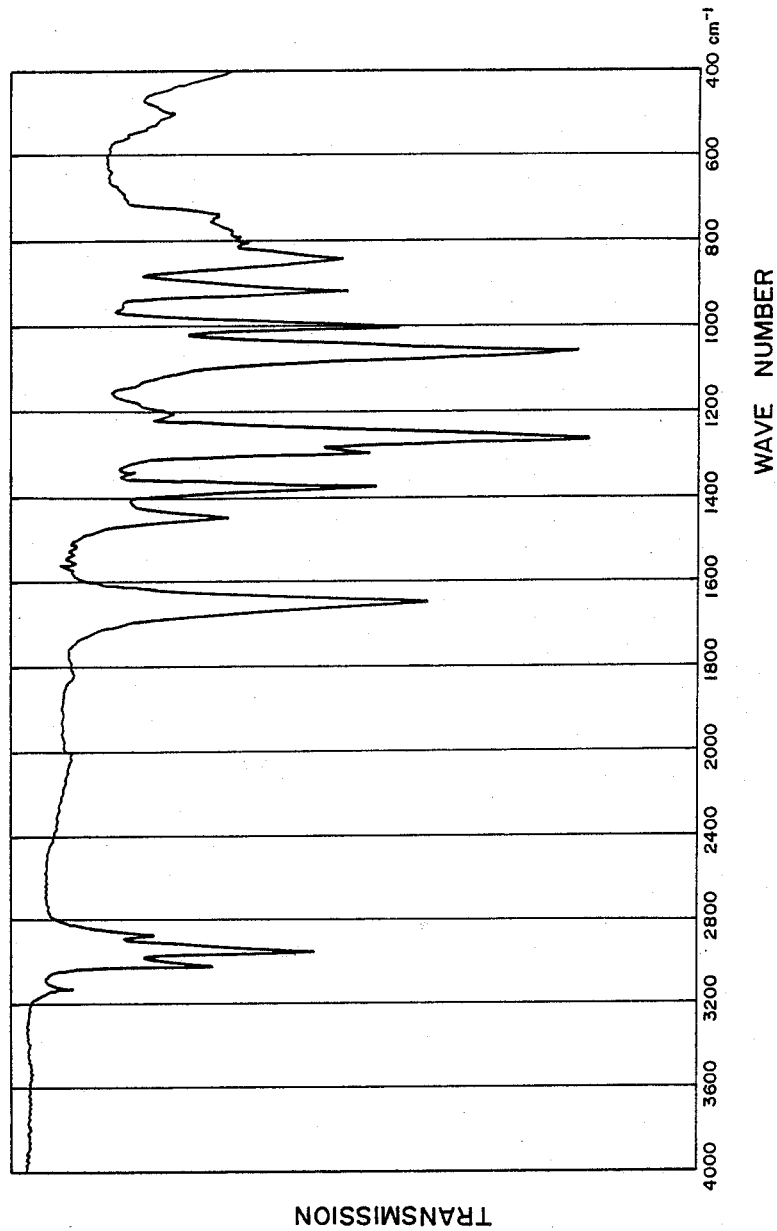

The above mentioned yield of the product was 55% of the theoretical value. FIG. 2 of the accompanying drawing shows an infrared absorption spectrum of the compound.

What is claimed is:

1. An organosilicon compound represented by the general formula

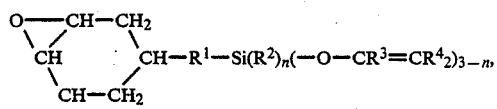

in which $R^1$ is $-CH_2-CH_2-$, $R^2$ and $R^3$ are each methyl, $R^4$ is hydrogen, and the subscript n is 0, 1, or 2.

2. The organosilicon compound as claimed in claim 1 which is a compound expressed by the formula

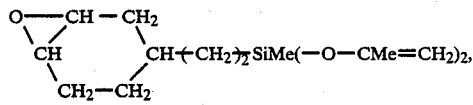

in which Me is a methyl group.

3. The organosilicon compound as claimed in claim 1 which is a compound expressed by the formula

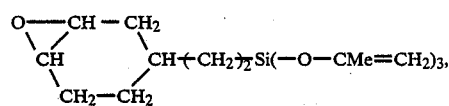

in which Me is a methyl group.

* * * * *